(12) United States Patent
Milleker et al.

(10) Patent No.: US 7,152,469 B2
(45) Date of Patent: Dec. 26, 2006

(54) FLUID FLOW SENSOR, METHOD AND SYSTEM

(75) Inventors: Anton Milleker, Largo, FL (US); Michael Rast, St. Petersburg, FL (US); Wayne B. Eubank, Clearwater, FL (US); Carlos Alberto Gonzalez, Clearwater, FL (US); Martin Greeley, Largo, FL (US); Diego Lasso, Seminole, FL (US); Govind Subramanian, Clearwater, FL (US)

(73) Assignees: Baxter International Inc., Deerfield, IL (US); Baxter Healthcare S.A., Wallisellen (CH)

( * ) Notice: Subject to any disclaimer, the term of this patent is extended or adjusted under 35 U.S.C. 154(b) by 300 days.

(21) Appl. No.: 10/757,337

(22) Filed: Jan. 13, 2004

(65) Prior Publication Data

US 2005/0154345 A1    Jul. 14, 2005

(51) Int. Cl.
*G01F 3/20* (2006.01)
(52) U.S. Cl. ..................................... 73/262
(58) Field of Classification Search ............. 73/861.56, 73/861.71, 239
See application file for complete search history.

(56) References Cited

U.S. PATENT DOCUMENTS

| | | | |
|---|---|---|---|
| 3,224,279 A | 12/1965 | Galli et al. | |
| 3,872,304 A | 3/1975 | Little et al. | |
| 3,897,682 A | 8/1975 | Brooks | |
| 3,940,609 A | 2/1976 | Johnstun | |
| 4,041,756 A * | 8/1977 | Head et al. ............... | 73/861.71 |
| 4,271,701 A | 6/1981 | Dempster et al. | |
| 4,307,618 A | 12/1981 | James et al. | |
| 4,376,390 A | 3/1983 | Rines | |
| 4,377,090 A | 3/1983 | Seulen | |
| 4,387,715 A | 6/1983 | Hakim et al. | |
| 4,419,895 A | 12/1983 | Fuller | |
| 4,472,022 A | 9/1984 | Bearcroft et al. | |
| 4,593,555 A | 6/1986 | Krutz et al. | |
| 4,679,029 A | 7/1987 | Krohn et al. | |
| 4,694,161 A | 9/1987 | Sackett | |
| 4,718,276 A | 1/1988 | Laughlin | |

(Continued)

FOREIGN PATENT DOCUMENTS

EP    0 221 733    10/1986

(Continued)

OTHER PUBLICATIONS

LMS MediFlo™ Advertisement written by www.siliconelms.com/LMS%20MediFLo.htm, printed on Jan. 12, 2004.

(Continued)

*Primary Examiner*—Harshad Patel
(74) *Attorney, Agent, or Firm*—Joseph P. Reagen; Bell, Boyd & Lloyd LLC

(57) ABSTRACT

A fluid flow sensor, a method of detecting flow/no flow and flow systems employing same are provided. In one embodiment, an infrared light emitting diode ("LED"), phototransistor, rigid housing and a flexible opaque diaphragm are used. The diaphragm opens upon a certain pressure and closes when that pressure is no longer present. The infrared LED is located at one end of a flow sensor, while the phototransistor is located at the opposite end. The flexible opaque diaphragm is located between the LED and the phototransistor. When flow is initiated, the diaphragm is pushed open allowing light from the infrared LED to pass through and be detected by the phototransistor. When flow is stopped, the diaphragm returns to the closed position and light no longer is allowed to pass through and therefore is not detected by the phototransistor.

38 Claims, 10 Drawing Sheets

U.S. PATENT DOCUMENTS

| | | |
|---|---|---|
| 4,756,274 A | 7/1988 | Rubino |
| 4,797,655 A | 1/1989 | Orndal et al. |
| 4,859,319 A | 8/1989 | Borsari |
| 4,864,870 A | 9/1989 | Payne et al. |
| 4,945,344 A | 7/1990 | Farrell et al. |
| 4,976,157 A | 12/1990 | Berthold et al. |
| 5,013,488 A * | 5/1991 | Abadi et al. ............... 261/70 |
| 5,039,279 A | 8/1991 | Natwick et al. |
| 5,049,860 A | 9/1991 | Farrell et al. |
| 5,120,951 A | 6/1992 | Small |
| 5,180,287 A | 1/1993 | Natwick et al. |
| 5,200,627 A | 4/1993 | Chevallet |
| 5,213,236 A | 5/1993 | Brown et al. |
| 5,339,995 A | 8/1994 | Brown et al. |
| 5,377,877 A | 1/1995 | Brown et al. |
| 5,392,648 A * | 2/1995 | Robertson ................... 73/239 |
| 5,409,144 A | 4/1995 | Brown |
| 5,439,143 A | 8/1995 | Brown et al. |
| 5,690,831 A | 11/1997 | Kenley et al. |
| 5,827,976 A | 10/1998 | Stouffer et al. |
| 5,911,219 A * | 6/1999 | Aylsworth et al. ....... 73/861.56 |
| 6,009,762 A | 1/2000 | Ockleston |
| 6,044,691 A | 4/2000 | Kenley et al. |
| 6,126,831 A | 10/2000 | Goldau et al. |
| 6,156,002 A | 12/2000 | Polaschegg et al. |
| 6,176,847 B1 | 1/2001 | Humphreys, Jr. et al. |
| 6,217,539 B1 | 4/2001 | Goldau |
| 6,239,446 B1 | 5/2001 | Cholin |
| 6,321,604 B1 | 11/2001 | Jackson et al. |
| 6,369,881 B1 | 4/2002 | Wang |
| 6,493,068 B1 | 12/2002 | Barrows |
| 6,611,319 B1 | 8/2003 | Wang |
| 6,668,643 B1 * | 12/2003 | Pettinaroli et al. ............ 73/239 |
| 2002/0024666 A1 | 2/2002 | Thomasson et al. |
| 2002/0186140 A1 | 12/2002 | Anderson |

FOREIGN PATENT DOCUMENTS

| | | |
|---|---|---|
| EP | 0 321 754 | 1/1988 |
| EP | 0 298 587 A2 | 1/1989 |
| EP | 0 547 210 | 3/1992 |
| EP | 0 497 195 A1 | 8/1992 |
| EP | 0 845 273 | 11/1997 |
| EP | 0 900 094 | 1/1998 |
| EP | 1 324 011 | 12/2002 |
| WO | WO 00/15278 | 3/2000 |
| WO | WO 01/65234 | 9/2001 |

OTHER PUBLICATIONS

LMS Manufacturing Advertisement written by www.siliconelms.com/manufacturing.htm, printed on Jan. 12, 2004.

International Search Report for PCT/US2004/042573 mailed May 25, 2005.

Written Opinion of The International Searching Authority for PCT/US2004/042573.

* cited by examiner

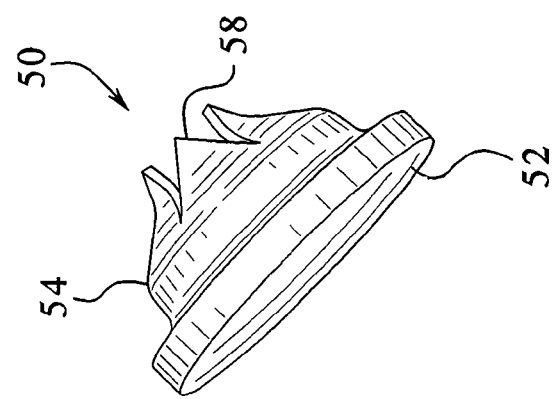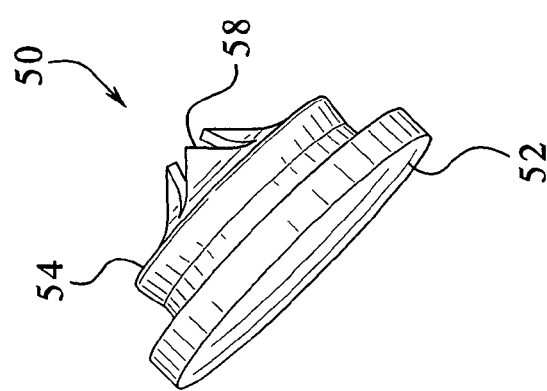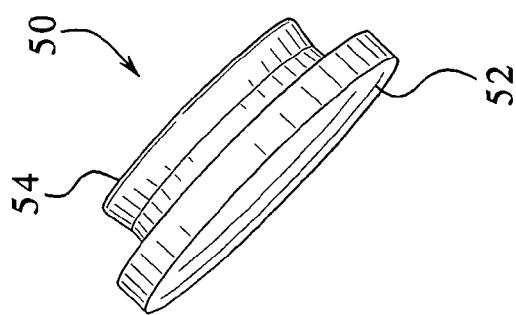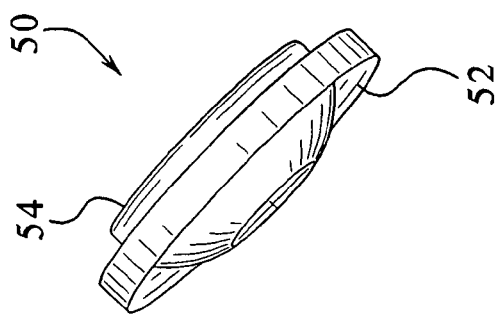

FLUID FLOW SENSOR, METHOD AND SYSTEM

BACKGROUND OF THE INVENTION

There are many important safety concerns with medical fluid systems. One important safety concern in connection with medical fluid systems, especially those transferring drugs or fluids to and from a patient, is the need to ensure that the medication or fluid is traveling to the appropriate place at the appropriate time. A number of conditions can arise to disrupt the proper flow of fluid within a medical fluid system. For instance, even if the system is otherwise operating properly, the lines to and from the pump may become kinked or otherwise obstructed, for example, due to the patient rolling over onto a line.

Another concern with fluid flow systems, especially larger systems, is to ensure that its myriad of valves are working properly, e.g., are not leaking and are not blocked. Larger systems, such as the System 1000® hemodialysis/hemofiltration machine produced by the assignee of the present invention, include many valves, some of which are pivotal to the operation and safety of the machine. For instance, there are valves that operate with the fluid pumps that either direct fluid from a source to the patient (e.g., to the patient's blood line) or from the patient to drain. Also, in hemodialysis and hemofiltration operations, a net amount of fluid called ultrafiltrate ("UF") is removed from the patient over the course of therapy. Certain valves play a critical role in operating with a UF metering device to ensure that the correct amount of fluid is taken from the patient. In any of those situations, a faltering valve can have adverse effects.

To ensure that fluid is flowing in medical fluid systems, flow sensors are employed. The flow sensors operate with a system controller to ensure, in critical situations, that fluid flow is present in a line when it supposed to be present and is not present when, for example, a valve is supposed to be closed. The flow sensor sends a signal indicating whether there is flow or no flow and in certain cases how much flow. The controller compares the signal outcome to an expected outcome and either allows the system to continue functioning if the actual outcome matches the expected outcome or commands an evasive action or alarm to occur if the actual outcome is different than the expected outcome.

Known fluid flow sensors have included a temperature sensitive device positioned in the fluid flow path, wherein the device is connected in a circuit. The temperature sensitive device, such as a thermistor, responds to temperature changes associated with fluid flow changes to produce a change in the circuit. The circuit change signals a certain response, for instance, an alarm to the controller. Temperature based flow sensors have had certain historical disadvantages due to their poor sensitivity to temperature changes, slow response time, fragility (the sensors typically contain a glass bead) and difficulty in being manufactured. Those disadvantages in certain instances have compromised the reliability of the fluid systems employing those sensors.

Accordingly, an improved flow sensing apparatus for medical fluid systems is needed.

SUMMARY OF THE INVENTION

The present invention provides a flow sensor, a method of flow sensing and flow systems employing same. The flow sensor and method are well suited for liquid systems, including medical fluid systems. It should be appreciated, however, that the sensor is expressly not limited to medical systems but is applicable in many different industrial uses, such as in food and beverage applications, chemical applications, industrial gas (e.g., nitrogen, oxygen, argon, carbon dioxide) applications, natural gas and petroleum applications, hydraulic or pneumatic applications, as well as others.

The flow method uses pressure exerted by the flow of a gas or liquid fluid. In one embodiment, the sensor includes a member that is maintained within a housing. The member moves when flow of a fluid occurs. The movement of the member enables the output of a source to be sensed by a receiver of the output of the source. In one example, the source is a light source and the receiver is a light detector, such as a phototransistor. It should be appreciated however that the present invention, and in particular its methodology, is expressly not limited to using a light source and light detection but instead can apply other types of sources and receivers and sensing mechanisms to detect flow when the member of the sensor has been moved by such flow.

In one embodiment, the sensor includes two housing portions that couple together around a flexible diaphragm. The diaphragm includes a slit or a series of slits, which enable liquid or gas to move through the diaphragm. When those slits are opened, light from a light source, such as an infrared light source, passes through the diaphragm so that a light receiver, such as a phototransistor can receive such light. The diaphragm is opaque or at least partially opaque so that when the slits are closed, light from the source does not pass through or does not readily pass through the diaphragm.

The mating housings define at their distal ends, circuit board carriers that receive small circuit boards with light emitting and light detecting electronics placed respectively thereon. Power is brought to the circuit boards from a power source, such as a regulated power supply, power supply printed circuit board, power transformer and the like.

The mating housing portions are held together and the boards are fixed to the housings, in one embodiment, via spring-like retainers, which slide in and out of the housing portions, snapping in and out of place. The distal ends of the housings or carriers are then potted or filled with a suitable adhesive or epoxy, so that the retainers cannot be readily removed, and so that the associated electronics cannot be touched or manipulated.

The sensor and its method of operation are useful in a plurality of different types of applications. The sensor can be used as a flow/no flow type sensor, which detects either the presence or absence of flow. The output can then be used by a controller or software to create an alarm condition either when a flow or no flow signal is outputted. Alternatively, the sensor includes an output that varies based on the amount of light or other physical phenomenon sensed, which is correlated to the amount of fluid flowing through the sensor.

One particularly useful application for the sensor and method of the present invention is to detect if a valve is leaking or stuck. For example, in the System 1000® hemodialysis/hemofiltration machine discussed above, a valve is closed at the end of a pump to patient stroke. If the valve does not close properly or is leaking, an uncontrolled flow of dialysate will flow to the patient. The sensor ensures that no flow is occurring at the end of the stroke and sends a suitable signal to the machine controller if flow is sensed. In the case of a stuck valve, full flow can occur. In the case of a leaking valve, however, only a small amount of fluid may be flowing. The sensor and method of the present invention are adaptable to provide a varying output to detect and communicate that a very small amount or percentage of fluid is flowing, e.g., leaking. Another medical application for the variable output sensor is to determine that a proper amount of a medication is being delivered to the patient.

It is therefore an advantage of the present invention to provide a flow sensor with a simplified apparatus and method of operation.

It is another advantage of the present invention to provide a flow sensor with an output flexible to be used in flow/no flow and variable flow applications.

It is a further advantage of the present invention to provide a flow sensor that is relatively inexpensive.

It is yet another advantage of the present invention to provide a flow sensor and method of flow sensing that is scaleable to be used in many different types of applications.

Moreover, it is an advantage of the present invention to provide a flow sensor that can sense the flow of gas or liquid.

Still further it is an advantage of the present invention to provide a flow sensor that can be used in a sterilized medical environment.

Additional features and advantages of the present invention are described in, and will be apparent from, the following Detailed Description of the Invention and the figures.

BRIEF DESCRIPTION OF THE FIGURES

FIGS. 6A to 6E are perspective views of one embodiment of the diaphragm of the present invention in various stages of use.

DETAILED DESCRIPTION OF THE INVENTION

The present invention includes various flow sensors employing a method of sensing fluid flow that can detect whether fluid, no fluid or a variable amount of fluid is flowing through a flow path. As used herein, the term "fluid" includes both liquids and gases. That is, the flow sensor of the present invention is operable with liquid, gas and multi-phase systems. In particular, the flow sensor is well suited for liquid systems, including medical fluid systems. It should be appreciated, however, that the sensor is expressly not limited to medical systems but is applicable in many different industrial uses, such as in food and beverage applications, chemical applications, industrial gas (e.g., nitrogen, oxygen, argon, carbon dioxide) applications, natural gas and petroleum applications, hydraulic or pneumatic applications, as well as others.

The sensor makes use of the fact that the flow of fluid under pressure exerts a force along the walls of the tubing, piping or other type of fluid flow conduit that it contacts. That force is able to move an object or member. The movement of the object or member enables a physical phenomenon, e.g., light, heat, electricity, force or pressure, to be detected. That detection can then be interpreted to mean that either fluid is flowing when it is supposed to be flowing or flowing when it is not supposed to be flowing. Alternatively, if there is no flow, the member does not move and an appropriate signal is sent accordingly. That signal can then be interpreted to mean that either fluid is not flowing when it is supposed to be flowing or not flowing when it is not supposed to be flowing.

Figure 1:
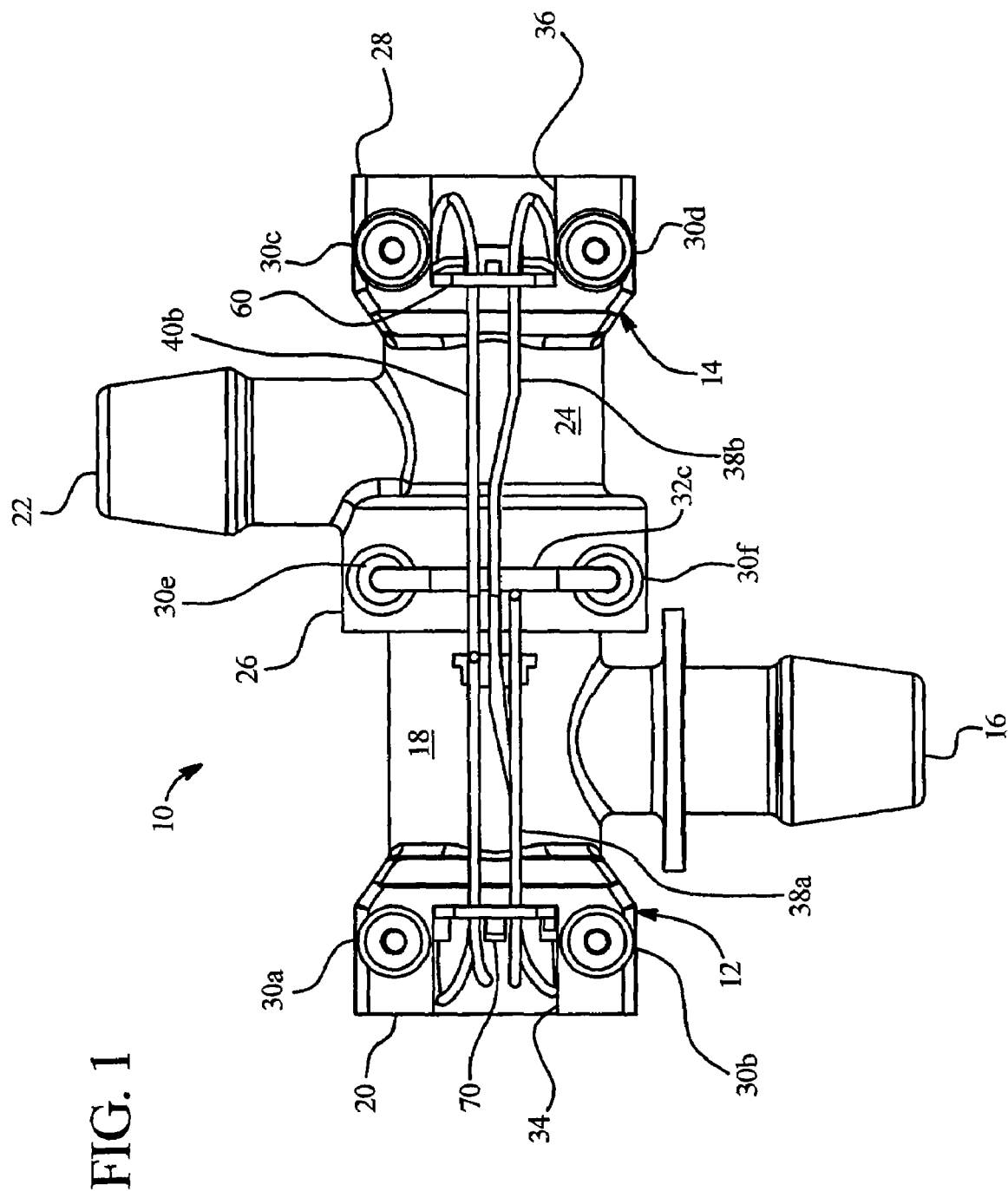
FIGS. 1 to 3 are various assembled views of one embodiment of a flow sensor of the present invention.
Figure 2:
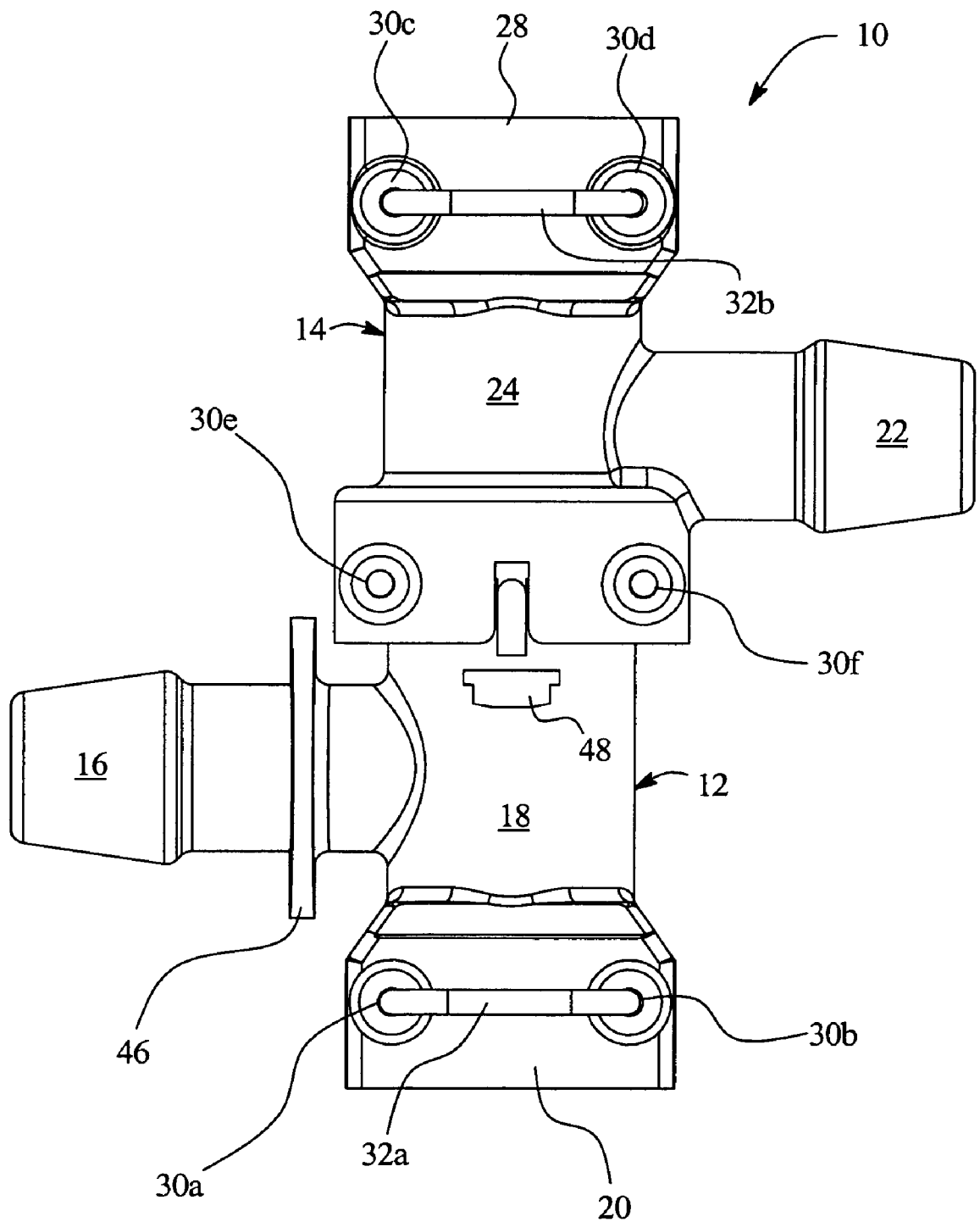
Figure 3:
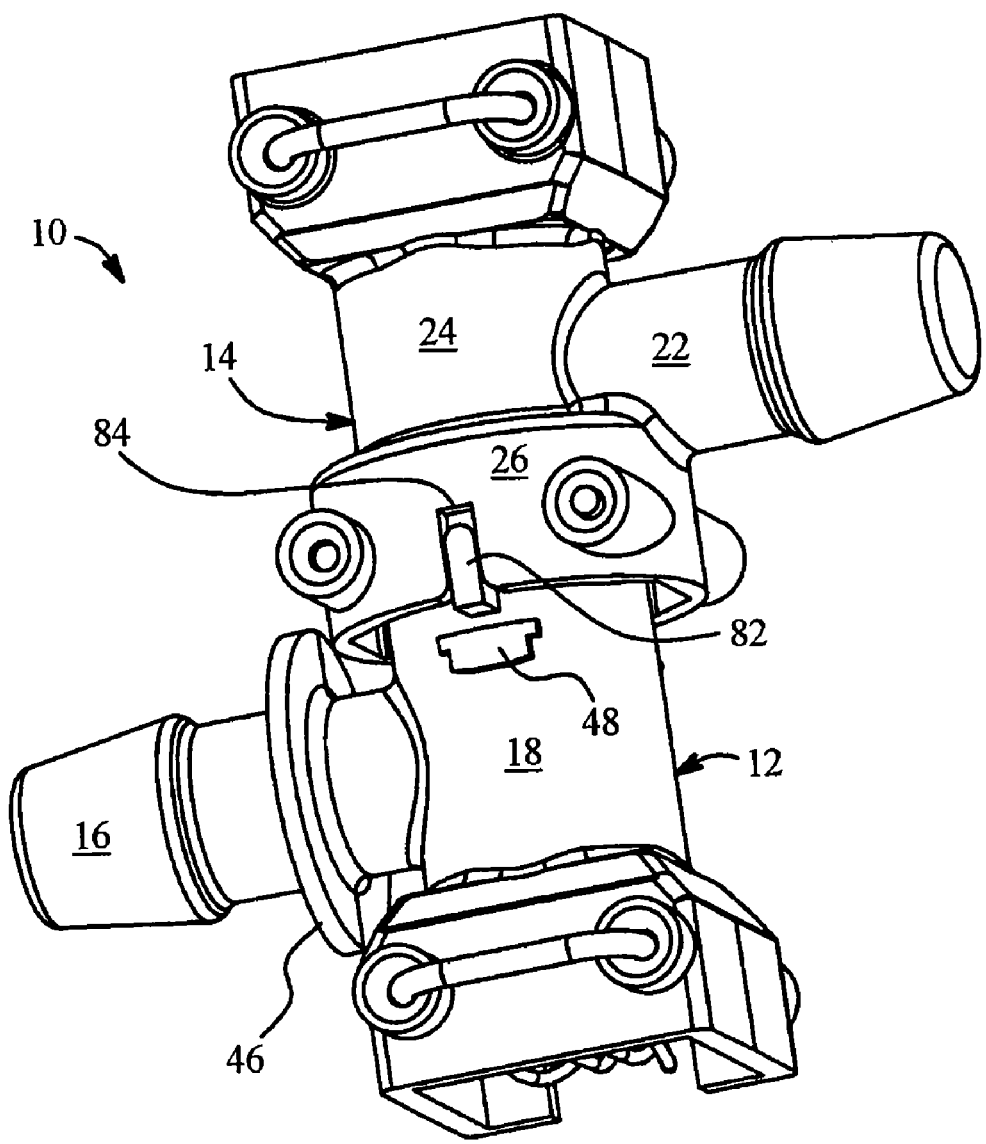

Referring now to the drawings and in particular to FIGS. 1 to 3, one embodiment of an assembled flow sensor 10 employing the methodology of the present invention is illustrated. FIGS. 1 and 2 illustrate sensor 10 from opposite sides. FIG. 3 highlights the connection between a male housing portion 12 and a female housing portion 14. The illustrated sensor 10 is particularly well suited for medical fluid flow applications. It should be appreciated, however, that the concepts discussed with respect sensor 10 are applicable to the different types of applications described above.

Housing portions 12 and 14 of sensor 10 are plastic in one embodiment, such as acrylic, delorin, an FDA approved plastic, kel-f, a high temperature plastic, nylon, phenolic, polysulfone, polycarbonate, polyester, polyethylene, polypropylene, polystyrene, polyvinylchloride, polyvinylidene fluoride and combinations thereof. Alternatively the portions 12 and 14 are made of any suitable metal, such as brass, copper, steel, stainless steel, aluminum and combinations or alloys thereof. Portions 12 and 14 are alternatively ceramic or any other suitable material. Portions 12 and 14 can be made of the same or different materials and individually can be made of any combination of the above materials.

Male housing portion 12 defines or includes a connector 16, which extends from a tube section 18. A diaphragm holder 42 (seen in FIG. 4, which shows male housing portion 12 by itself) resides at a mating end of tube section 18. A circuit board carrier 20 resides at the distal end of tube section 18.

Female housing portion 14, in turn, includes or defines a connector 22, which extends from a tube section 24. A female adapter 26 is defined at the mating end of tube section 24. Adapter 26 of female housing portion 14 fits over the diaphragm holder 42 of male housing portion 12 in the assembled views of FIGS. 1 to 3. Female housing portion 14 further includes or defines its own circuit board carrier 28 at the distal end of tube section 24.

Circuit board carrier 20 of male housing portion 12 defines a pair of retainer insertion apertures 30a and 30b. Retainer insertion apertures 30a and 30b receive a retainer 32a, as seen in FIG. 2. Retainer 32a holds, at least initially, a light-detecting printed circuit board ("PCB") 70 in place. PCB 70 is illustrated and discussed below in more detail in connection with FIGS. 8 and 9.

Circuit board carrier 28 of female housing portion 14 defines a pair of carrier receiving apertures 30c and 30d. FIG. 2 illustrates that apertures 30c and 30d receive a retainer 32b, which holds a light-emitting printed circuit board 60 in place. Again, PCB 60 is illustrated and discussed below in more detail in connection with FIGS. 8 and 9.

The circuit board carriers 20 and 28 each include an inner wall or window (not illustrated) located approximately at the interface between the circuit board carriers and their respective tube sections 18 and 24. The inner walls or windows cap the ends of sensor 10 at the insides of carriers 20 and 28, so that the insides of housing portions 12 and 14 are sealed to enable fluid to flow through sensor 10 without leaking. A light source and light detector, as discussed below, are placed just outside of and face inwards towards the respective windows for efficient transmission and reception of light energy.

The inner walls or windows are translucent or transparent and enable at least certain types of light to pass from the outside of the transmitting window, through housings 12 and 14, and from inside sensor 10 through the receiving window. The printed circuit boards are placed at the distal ends of tube sections 18 and 24, substantially parallel with the windows, and into the openings defined by carriers 20 and 28. The retainers 32a and 32b are then fitted into the respective apertures 30 (collectively referring to any one, combination of or all of the apertures 30a to 30f), so that the PCBs 60 and 70 cannot come loose or move translationally away from carriers 20 and 28.

Carrier 20 defines a notch 34, while carrier 28 defines a notch 36. Notches 34 and 36 enable hot and neutral power wires 38a, 38b and 40a, 40b, respectively, to extend from the PCBs 60 and 70, through the notches 34 and 36 of circuit board carriers 20 and 28, instead of having to make a sharp bend out the openings thereof.

Male and female housings 12 and 14 are connected together using a similar apparatus that holds the PCBs in the carriers 20 and 28. In the illustrated embodiment, female housing 14 defines retainer receiving apertures 30e and 30f. Apertures 30e and 30f receive a retainer 32c, which holds the housing portions 12 and 14 tightly together.

FIG. 3 also illustrates that tube section 18 of housing portion 12 defines a key 82 that is received by a notch 84, where notch 84 is defined by adapter 26 of female housing portion 14. Key 82 and notch 84 ensure that connectors 16 and 22 of portions 12 and 14, respectively, are oriented properly when the housing portions are assembled. As illustrated, sensor 10 creates a slight jog for the fluid flowing through the sensor, but sensor 10 is otherwise a relatively in-line device that does not produce a significant pressure drop.

Figure 4:
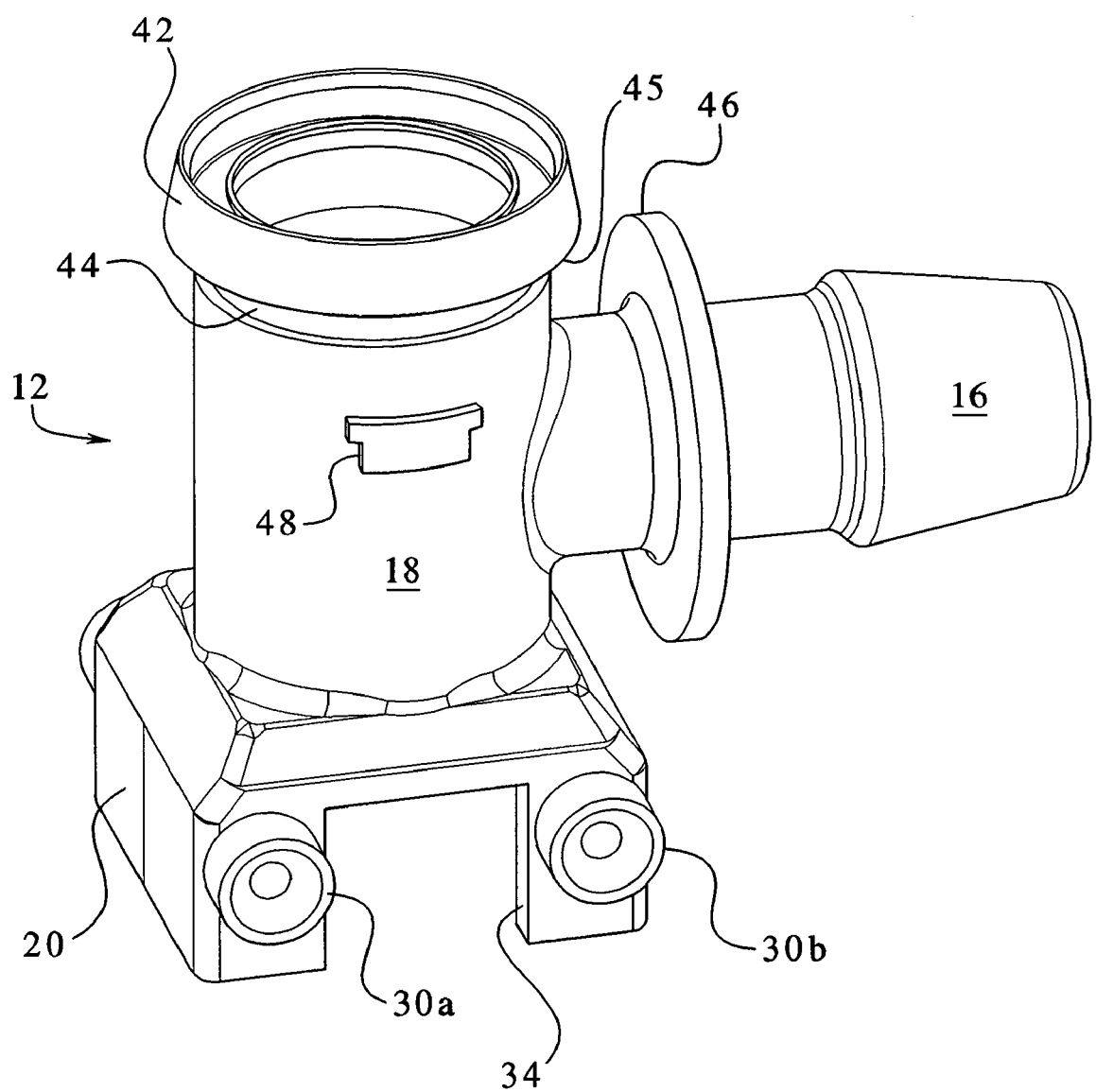
FIG. 4 is a perspective view of one embodiment of a housing portion of the flow sensor of the present invention.

Referring additionally to FIG. 4, male housing portion 12 is shown separate from the rest of the sensor 10. Diaphragm holder 42 is positioned at the mating and opposite end of tube section 18 from circuit board carrier 20. Diaphragm holder 42 as illustrated tapers to an edge. That edge engages and abuts against an inner surface of adapter 26 of female housing 14 when housings 12 and 14 are compressed together. The edge ensures that a compressible and sealable diaphragm 50 sandwiched between the housings is not overly compressed when housings 12 and 14 are mated.

A groove 44 is machined or provided in tube section 18 directly behind or below diaphragm holder 42. When male housing portion 12 is sealingly mated with female housing portion 14, groove 44 is substantially in alignment with the retainer insertion apertures 30e and 30f. In that manner, when retainer 32c is inserted through apertures 30e and 30f, retainer 32c is also inserted through groove 44, which locks male portion 12 and female portion 14 sealingly together. That is, retainer 32c catches the lip 45 of diaphragm holder 42 if someone attempts to pull housing portions 12 and 14 apart while retainer 32c is in place.

In alternative embodiments, the housing portions 12 and 14 are connected via a threaded connection, a compression connection, a quick disconnect connection or any other suitable type of tubing or piping connection. Certain of those alternative types of connections may be better suited for higher pressure applications. It is also possible to place the diaphragm 50 in a separate housing or fitting, such as a male pipe nipple or female coupling, and connect that fitting to female or male threaded housing portions 12 and 14, respectively. Or, the separate diaphragm housing could have tube ends and connect to housings 12 and 14 via tube connectors.

Male housing portion 12 also includes various apparatuses for communication with the user. For instance, male portion 12 includes or defines a barb flange 46 that indicates to the operator that the component is the male portion 12. This is important once the portions 12 and 14 are fitted together, wherein it may be difficult to discern which portion includes diaphragm holder 42 and which portion includes female adapter 26. It is important to know male from female because sensor 10 operates properly when the detection board 70 (FIG. 8) is placed into the male PCB carrier 20 and the LED board 60 is placed into the female carrier 28.

Figure 5:
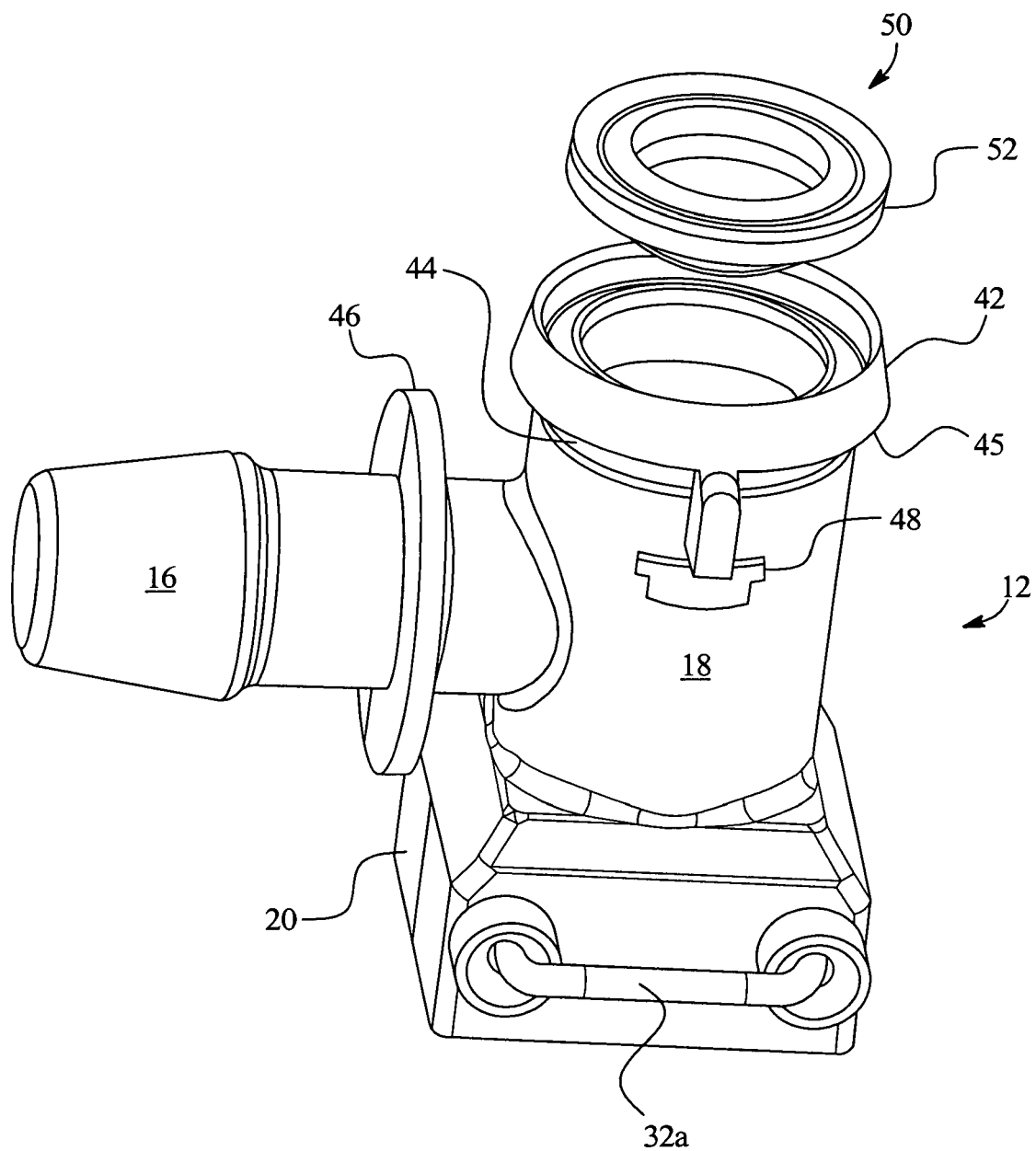
FIG. 5 is a perspective view of one embodiment of the housing portion of FIG. 4, which is about to receive a diaphragm of the present invention.
Figure 6A:
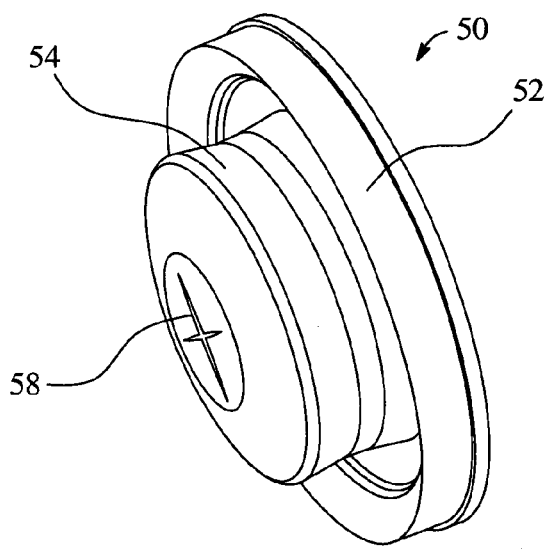
Figure 7:
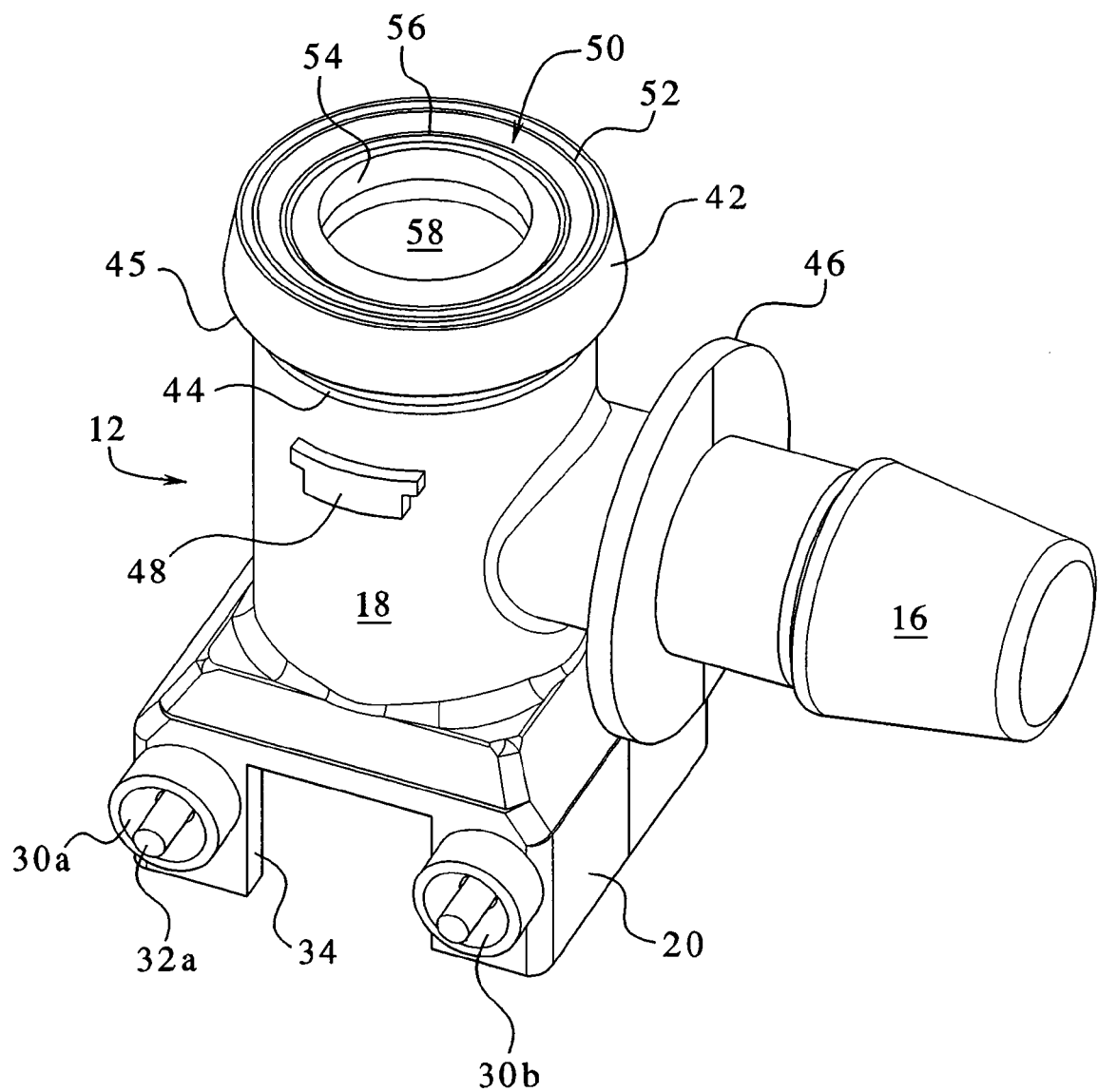
FIG. 7 is a different perspective view of the housing portion of FIG. 4 showing a reverse side of the diaphragm of FIG. 6 mounted inside the portion.

Tube section 18 of housing portion 12 also includes or defines a diaphragm mounting indicator 48, which is shaped and oriented to show the proper placement and positioning of a diaphragm 50 shown in FIGS. 5 to 7. FIGS. 5 to 7 illustrate the placement, configuration and operation of diaphragm 50. FIG. 5 illustrates diaphragm 50, which is just about to be placed inside diaphragm holder 42 of male housing portion 12. FIG. 6A illustrates that diaphragm 50 has a hat-type shape with a rim 52 and a stem 54. Indicator 48 in FIG. 4 is oriented so that its representative stem portion faces towards carrier 20, indicating the direction with which the stem 54 of diaphragm 50 should be placed into diaphragm holder 42 of male portion 12.

FIG. 6A illustrates diaphragm 50 in a closed or no flow state. FIGS. 6B and 6C illustrate stem 54 being pushed through or rolling inside of rim 52 due to pressure of a fluid. FIG. 6D illustrates diaphragm 50 in a mid or intermediate flow state, wherein septum 58 is partially opened and stem 54 is partially inverted. FIG. 6E illustrates diaphragm 50 in full flow state, wherein septum 58 is fully opened and stem 54 is more fully inverted. At this point, flow and/or pressure can increase further without septum 58 opening any further, such as in an on/off type of application. When flow stops and the force of moving fluid is removed, the natural springiness of the shape and material of diaphragm 50 causes the diaphragm to return to the form as seen in FIG. 6A.

FIG. 7 illustrates the opposite side of diaphragm 50 than the side shown FIGS. 6A and 6C. This opposite side includes or defines a sealing groove 56. Sealing groove 56 is defined or provided at least in part by rim 52 of diaphragm 50. Sealing groove 56 receives a mating annular or tubular member (not illustrated) from female housing portion 14 when engaged to portion 12, so that a liquid-tight or air-tight seal is made between the two housing portions.

One suitable diaphragm 50 is a V8 style diaphragm provided by Liquid Molding Systems of Midland, Mich. The V8 style diaphragm requires a 0.5 psig pressure differential to open a septum 58 defined by the face of stem 54. Septum 58 in the illustrated embodiment includes a pair of perpendicularly positioned slits, which can be 250 thousandths by 100 thousandths of an inch in length. It should be appreciated however that septum 58 can include other suitably shaped or sized openings that enable fluid to flow through diaphragm 50, and which close upon the stoppage of flow. Other starting pressures could be used to open or crack the diaphragm depending on the application. In the illustrated embodiment, diaphragm 50 does not create a significant pressure drop.

In many applications, it does not matter which way the diaphragm is mounted in the flow path, meaning male housing 12 can be oriented upstream or downstream of female housing 14. Diaphragm 50 can be used bi-directionally. In other applications, such as low pressure differential applications, the orientation of diaphragm 50 does matter. In such cases, a suitable marker, such as barb flange 46 shown in FIGS. 4 and 5, can be provided to indicate that associated connector 16 should be connected to the fluid inlet. In alternative embodiments, the flow of light and the direction of fluid can be in the same or different directions.

Diaphragm 50, in one preferred embodiment, is made of a material suitable for sealing between the plastic male and female housings, such as plastic, rubber or sponge rubber. The material can be any suitable material, such as buna-n, butyl, ethylene propylene diene monomer, natural sponge rubber, neoprene, silicone, vinyl, viton, polyurethane, polyvinyl chloride, polyethylene, any combination thereof or any other suitable material. The material can also have multiple plies, be impregnated with desired additives and/or be coated with a foil, such as a metal foil. The material of diaphragm 50 is flexible and also resilient, so that when fluid flowing through sensor 10 causes the split septum 58 to open, septum 58 closes thereafter when the flow of fluid stops as discussed above.

The size of the opening of septum 58 of diaphragm 50 can limit the flowrate for systems employing sensor 10. The V8 style diaphragm 50 described above can handle liquid flow rates of about two ml/min to about 2000 ml/min or even higher. Gas flowrates will vary depending on the pressure inside the system. In general, the housings 12 and 14 of sensor 10 can be sized so that the sensor will not be the limiting flow or pressure component in either a liquid or gas application. Additionally, sensor 10 and diaphragm 50 can have any suitable size, construction and be of any necessary material and material thickness to accommodate a wide range of pressures and flowrates for liquid and gas systems.

Diaphragm 50 in operation with sensor 10 is opaque or at least semi-opaque to block all light or some light emanating via the light source from reaching the light detector when septum 58 is closed. Diaphragm 50 when used with an infrared LED 62 and infrared detector 72, discussed below, is in one preferred embodiment configured to block or at least partially block infrared light. In other applications described below, another physical phenomenon besides light is used alternatively. In such cases, diaphragm 50 can be translucent or transparent. Depending on the phenomenon employed, diaphragm 50 can be mildly to highly resistive with respect to the movement of energy for that phenomenon. For example, if the source is a heat source and the detector is a heat detector, diaphragm 50 can be made of a material that is relatively resistive to the transfer of heat.

Figure 8:
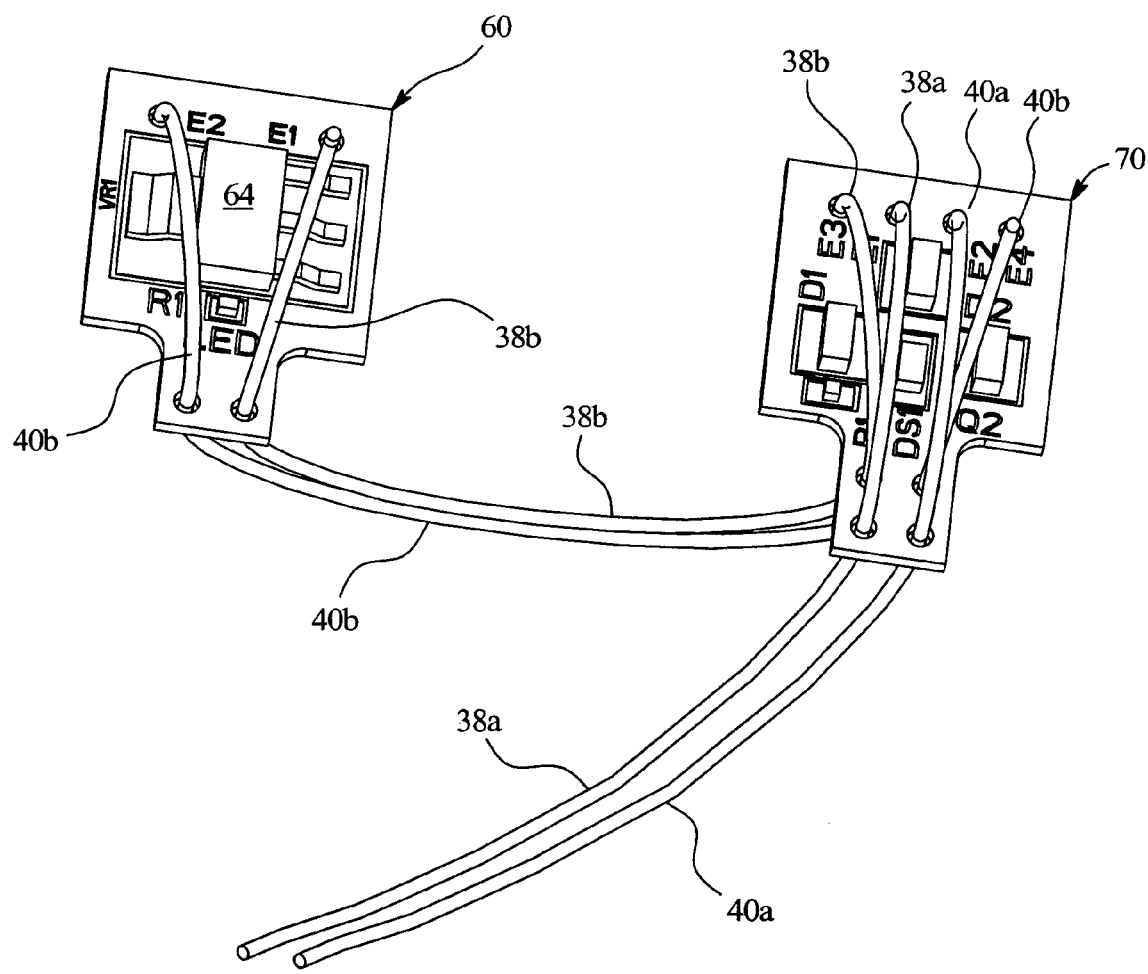
FIG. 8 is an illustration of the printed circuit boards and associated electronics used in one embodiment of the present invention.
Figure 9:
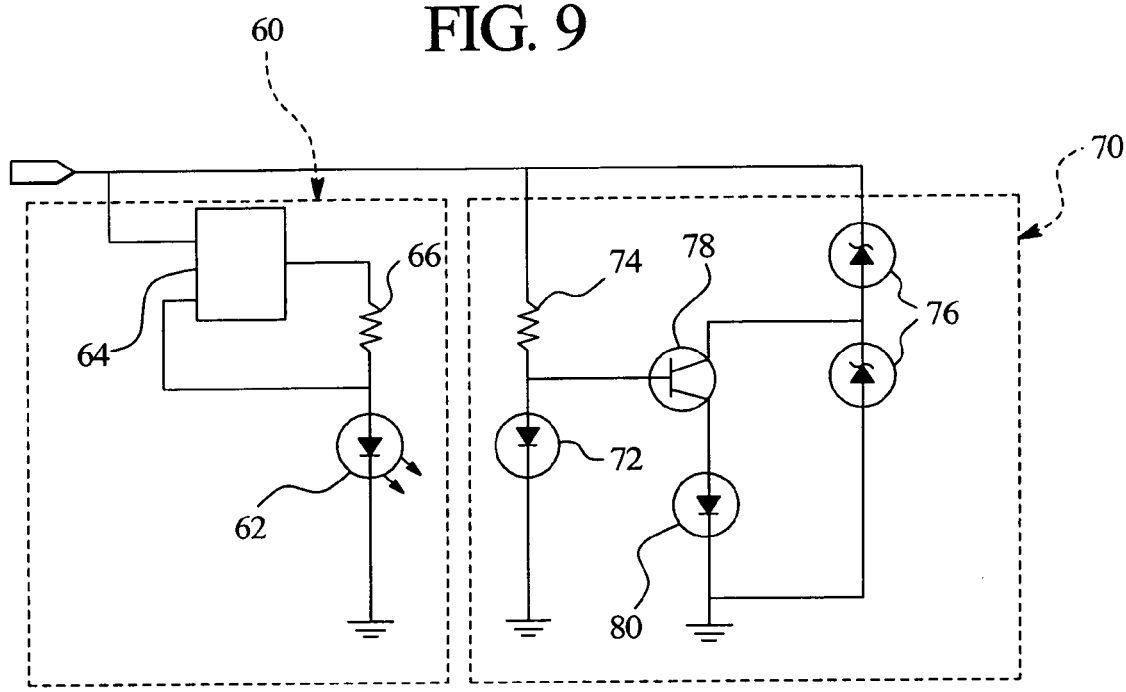
FIG. 9 is a schematic view of one embodiment of an electrical configuration of the present invention.

Referring now to FIGS. 8 and 9, one embodiment for each of the printed circuit boards 60 and 70 and the electrical schematic of flow sensor 10 is illustrated. FIG. 8 illustrates an LED board 60 and a detector board 70. Those boards 60 and 70 are shown superimposed in phantom lines in the electrical schematic of FIG. 9. FIG. 8 also illustrates that the PC boards 60 and 70 are connected to a power source via hot power wires 38a and 38b and neutral power wires 40a and 40b.

Board 60 is inserted into PC board carrier 28 through notch 36 of female housing portion 14. Afterward, retainer 32b is slid through apertures 30c and 30d to hold the board 60 in place. Detector board 70 is placed through notch 34 of carrier 20 of male housing portion 12, after which retaining ring 32a is positioned in openings 30a and 30b to hold board 70 in place. Although not illustrated, an adhesive, or epoxy, such as a Dymax™ adhesive, is applied on top of boards 60 and 70 and within the respective openings of carriers 20 and 28 to insulate the electronics, protect boards 60 and 70 and further hold same in place. Any suitable non-conductive material can be placed in the openings of carriers 20 and 28. Alternatively, a removable or fixed cap is placed over the ends of carriers 20 and 28 to encapsulate, cover and protect boards 60 and 70. The surfaces of PC boards 60 and 70 shown in FIG. 8, namely the surfaces to which the power wires are connected, face outward when mounted into sensor 10.

A light emitting diode 62, shown figuratively in FIG. 9, is placed on the side of PCB 60 that when it is mounted it faces inward towards the window of the respective carrier to which PCB 60 is mounted and towards the flow of fluid. Likewise, a phototransistor or detector 72, shown figuratively in FIG. 9, is placed on the side of PCB 70 such that when it is mounted in sensor 10 it faces inward towards the window of the respective carrier to which PCB 70 is mounted and towards the flow of fluid. Diode 62 and detector 72 are therefore not seen in FIG. 8.

Emitter 62 and detector 72 respectively emit and detect light towards and through the windows or translucent surfaces located at the base of carriers 20 and 28. LED 62 can be any suitable type of light emitting diode, a fiber optic source, any combination thereof as well as any other suitable type of light emitter. Detector 72 can be a phototransistor, an infrared light detector, a photodiode, a photovoltaic cell, any combination thereof as well as any other suitable type of light detector.

Power is brought from an outside source via hot and neutral wires 38a and 40a, respectively, to detector board 70 as illustrated in FIG. 8. The source can be any one or combination of a regulated power supply, power supply printed circuit board, power transformer and the like. Power is then split from detector board 70 to LED board 60 via hot and neutral wires 38b and 40b, respectively. In one embodiment, the power supply supplies eighteen milliamps to detector board 70, wherein some of that current is sent to LED board 60. LED board 60 also houses an integrated circuit, such as an IC regulator 64, and a resistor 66. Regulator 64 ensures that enough power is provided to LED 62 by limiting the amount of current used by detector board 70.

Detector board 70 also houses a resistor 74, a pair of diodes 76, a transistor 78 and an LED indicator 80. LED indicator 80 can be used, for example, to troubleshoot, to display whether sensor 10 is currently sensing a flow or a no flow condition, or to display whether sensor 10 is sensing an amount of flow above or below a preset threshold of flow.

An infrared LED 62 is preferred in certain medical uses relative to other types of LED's, such as ultraviolet LED's, because the wavelength of infrared light is well suited for those uses. For instance, with hemodialysis ("HD") or hemofiltration ("HF"), fluid in dialysate lines downstream from the dialyzer (HD) or carrying ultrafiltrate (HF) can be cloudy or milky and textured due to waste and toxins cleared from the patient's blood. Such cloudiness, etc., can at least partially block visible light from reaching a light sensor. It is therefore desirable in such applications to use infrared light, which operates in a wavelength range that travels through the dialysate without being effected by the patient's waste and toxins. Infrared light is also desirable for troubleshooting purposes because infrared detector 72 will not be falsely triggered when a panel of the machine is removed, allowing visible light to reach the detector. In other applications, infrared light may not be needed, and thus sensor 10 is expressly not limited to any particular bandwidth of light and can employ any suitable type of emitter and detector based on the type of application, cost, reliability, etc.

In operation, when liquid, gas or any combination thereof reaches a certain pressure inside the inlet side of sensor 10, for example 0.5 psig, the septum 58 of diaphragm 50 opens to enable the fluid to continue to flow through an associated flow path. At the same time, light, such as infrared light, is able to travel through housings 12 and 14 from emitter 62 to receiver 72, after which sensor 10 sends an appropriate output to a controller of the flow machine or to any suitable device for receiving the signal from sensor 10. Sensor 10 is operable to provide an on/off type flow or no flow electrical signal. In that scenario, the output of sensor 10 can be a de-energized output, e.g., no volts or no milliamps or low volts or low milliamps, upon a no flow or low pressure condition, e.g., at a zero pressure or a pressure below the cracking pressure of diaphragm 50. That output could be called a de-energized output. Here, when diaphragm 50 sees a threshold pressure, the pressure opens diaphragm 50, light is sensed and the electrical output increases to an on-state or fluid flow state, which includes an amount of volts or amps that is increased with respect to the off-state or the de-energized state. It is also possible that the reverse occurs, where the off-state includes a higher amount of volts or amps than does the on-state.

Sensor 10 is alternatively operable to provide a variable output based upon how much light is sensed by phototransistor 72. For example, sensor 10 can have an output range of approximately seven volts to about 13.8 volts, wherein seven volts corresponds to no light or low light and thus no pressure or low pressure, and wherein 13.8 volts corresponds to full saturated light or full flow or full pressure. A voltage output between seven and 13.8 volts corresponds to an intermediate amount of light and therefore an intermediate amount of flow. The voltage output in one embodiment increases linearly from seven volts to 13.8 volts based on increasing pressure or flowrate and an increase in the amount of light sensed. Again, it is also possible that a higher variable volt or milliamp output coincides alternatively with a lower flow or pressure and decreases, e.g., linearly, as flow or pressure and light sensed increases.

The applications of sensor 10 are many. For example, sensor 10 can be used in an on/off scenario, where the sensor output is used to detect a normal state when fluid is flowing or an alarm state when fluid is not flowing. Alternatively, the sensor output can be used in an on/off scenario to detect a normal state when fluid is not flowing and an alarm state when fluid is flowing. Examples of such a use are to verify that a valve has switched off when it is supposed to have switched off. Another use is to detect if a valve leaks. That is, when a valve is closed, the controller expects to see no flow downstream of the valve. If sensor 10 located downstream of the valve detects flow, the controller can determine that the valve is leaking or blocked and take appropriate action, such as shutting down a pump or portion of the system, closing a safety valve, triggering an audio, visual or audiovisual alarm and any combination of thereof.

Another use for sensor 10 is to detect an amount of a change in flowrate either from a lower to a higher flow rate or from a higher to a lower flow rate. For example, the controller or software can be configured to look for a certain amount of change in voltage from sensor 10, which corresponds to a certain amount of change in the amount of light detected and in the amount of flow through a path. If not enough change is sensed, the controller can take one or more of the above described appropriate actions. While voltage is used as an output in one embodiment, it is also possible to output current, such as milliamps.

Figure 10:
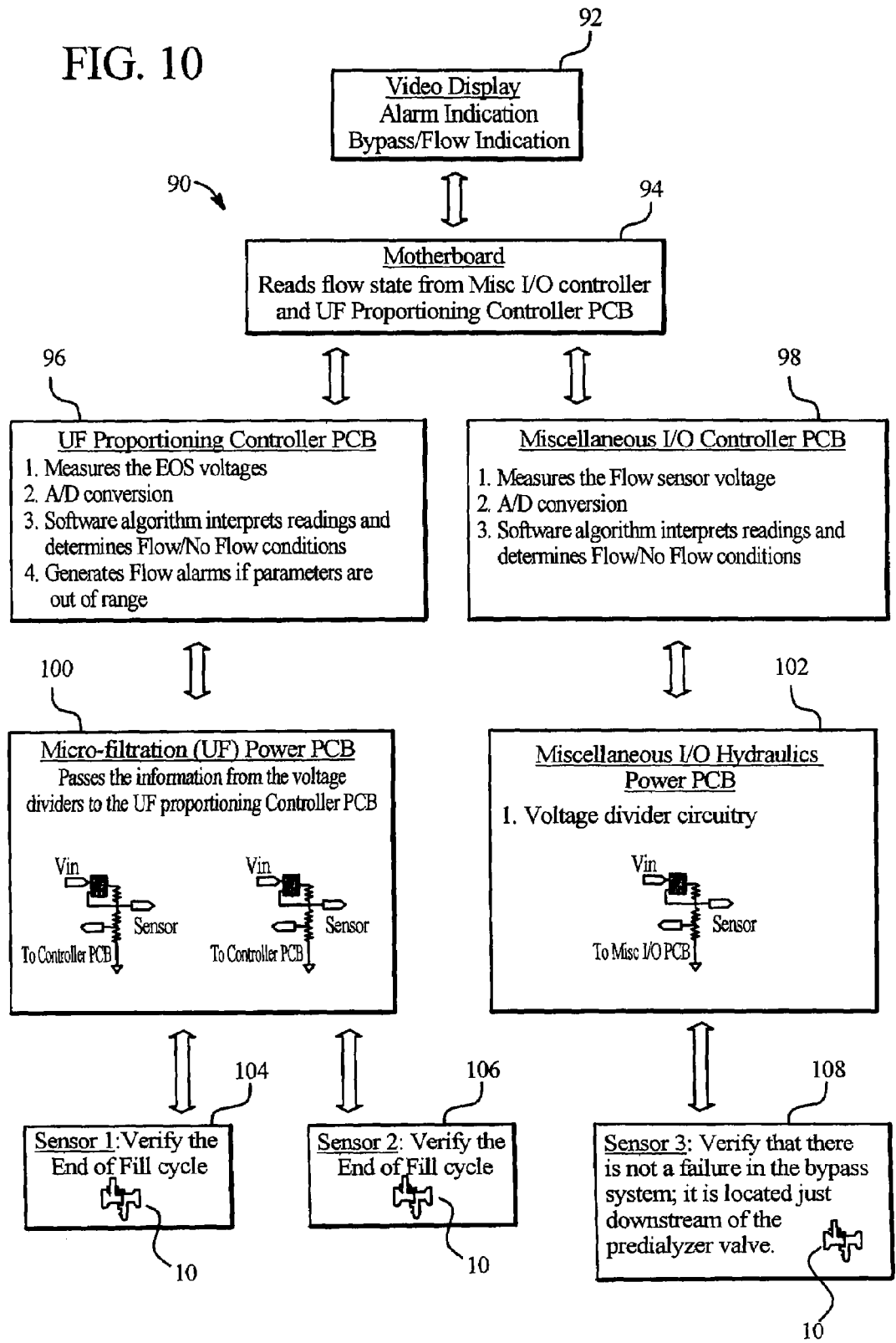
FIG. 10 is a schematic representation of a power and logic flow distribution for one application using multiple sensors and the methodology of the present invention.

Referring now to FIG. 10, a system 90 showing one power and logic distribution for employing the sensors 10 of the present invention is schematically illustrated. System 90 includes a video display illustrated at block 92 and a motherboard illustrated at block 94. The video display can show the patient or operator an alarm or a flow bypass condition as an output of the implementation of sensors 10 within system 90. The motherboard accepts information from delegate boards shown at blocks 96 and 98 and relays that information to the display in a form that can be converted to show an audio, visual or audiovisual message at the display.

The delegate boards in the illustrated embodiment are an ultrafiltrate proportioning control board 96 and a miscellaneous input/output control board 98. Each of those boards is responsible for controlling different tasks within a fluid flow machine, such as a medical fluid flow machine, e.g., an HD or HF machine. The delegate boards shown at blocks 96 and 98 are each operable to measure voltages sent from lower level printed circuit boards shown at blocks 100 and 102. The lower level boards send voltages to the delegate boards based on signals sent from the sensors 10. The voltages in one embodiment arrive at the delegate board in analog form and are measured and digitized at the delegate boards.

The delegate boards contain software that interprets the measured and digitized signals and in the illustrated embodiment make a flow or no flow determination based on the interpretations. At block 96, the UF board generates a flow alarm signal to the motherboard if the interpreted signals are out of range.

The lower level boards shown at blocks 100 and 102 include circuitry that accepts the signals from sensors 10 and converts the signals into a form that can be read by the delegate boards. In one embodiment, the voltage outputs of sensors 10 are scaled to a different voltage preferred by the delegate boards.

The sensors 10 are placed at desired locations within the machine. System 90 illustrates at blocks 104 that 106 that the sensors 10 are each placed in fluid communication with a different end of stroke ("EOS") valve. The separate strokes can be, for example, a "to patient stroke" and a "from patient stroke". Block 108 illustrates that sensor 10 is also placed in a drain line, between a predialyzer valve and the dialyzer, to ensure that in certain alarm situations fluid is being shunted away from the patient or dialyzer, and is instead being dumped to drain.

Figure 11:
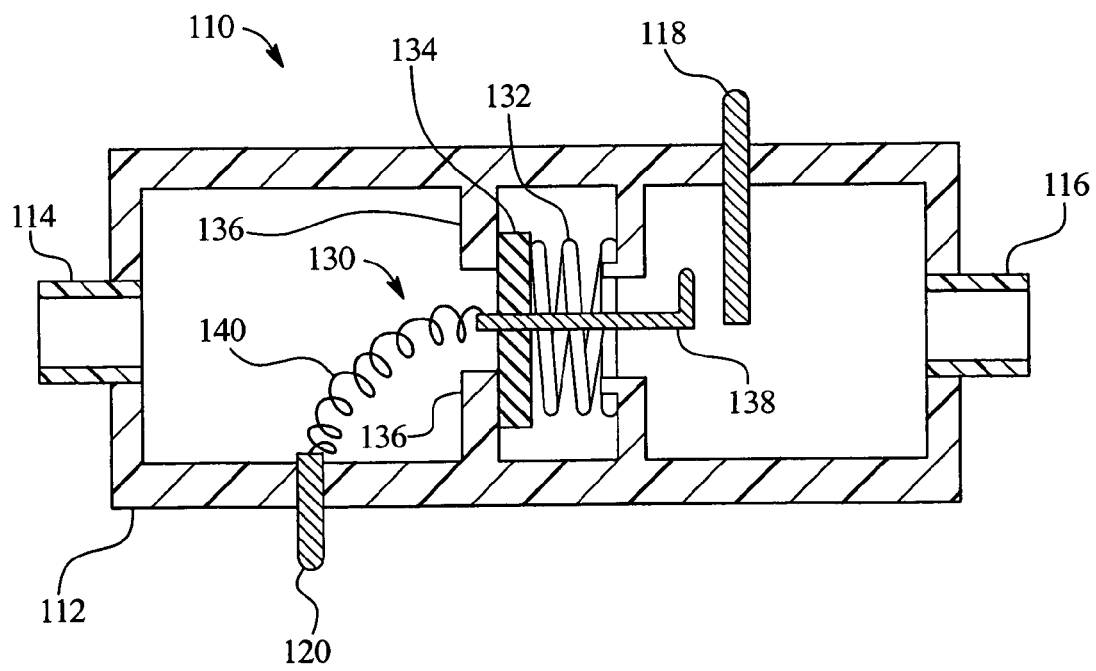
FIG. 11 is a sectioned view of an alternative apparatus for a flow sensor employing the methodology of the present invention.

Referring now to FIG. 11, an alternative sensor 110 is illustrated. Sensor 110 applies the same concepts and methodology described above in connection with sensor 10. Sensor 110 however employs a different apparatus for sensing when there is flow and no flow. Sensor 110 includes a housing 112, which can be a non-conductive or dielectric housing. Housing 112 includes connectors 114 and 116 that connect to a fluid flow path, such as a gas or liquid path. It should be appreciated that connectors 114 and 116 as well as connectors 16 and 22 described above in connection with sensor 10 can be any suitable type of gas or liquid connector, such as a tube connector, a male or female threaded connector, a hose barb connector, a quick-disconnect connector, any type of medical fluid connector and any combination thereof.

Sensor 110 includes a member 130 that functions the same operationally as diaphragm 50 described above. Member 130 opens when a flow condition or a suitable amount or flow or pressure is present. Member 130 is closed when no flow or low flow is present. Member 130 is closed and is held closed via a spring 132, which presses head 134 against a stop 136 defined by or provided by housing 112. Head 134 is connected to an electrode 138. When pressure inside housing 112 from fluid flowing through connector 114 reaches a point that it overcomes a spring force of spring 132, head 134 and electrode 138 move so that electrode 138 makes electrical contact with conductor 118.

Conductors 118 and 120 extend from housing 112. A flexible conductive cord 140 connects electrode 138 to conductor 120, so that a complete circuit between conductors 118 and 120 can be made when electrode 138 contacts conductor 118. That electrical connection can be used to send a signal to a controller or other suitable output device. That signal can be used in any of the manners described above. Although sensor 110 is shown as an on/off type of device, it is also possible to connect electrode 138 openably to a potentiometer or other type of variable or analog electrical component to create a voltage, milliamp or resistance output that varies based on the distance that head 134 and electrode 138 are moved. That distance in turn is dependent upon the amount of pressure and the amount of flow through sensor 110.

It should be appreciated that the concepts described in the present invention can be embodied in multiple forms, wherein each form takes advantage of the fact that fluid flowing through a sensor can create a force that moves a member, and wherein the movement of that member enables a sensing mechanism to provide a variable or on/off type of output. That is, the sensor of the present invention can be further adapted to operate not only based on a light emitter and receiver (sensor 10) and mechanical movement (sensor 110), but can also operate using other types of physical phenomena that change or are sensed based on the flow of a fluid and the opening and closing of a member based on the flow of the fluid. Such other phenomena include a change in temperature that is sensed across an insulative diaphragm. Further, a strain gauge could be used to sense the amount of force or pressure, for example, exhibited by a moving member. It is also possible to sense a change in capacitance based on a change in dielectric via the movement of the member.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

The invention is claimed as follows:

1. A flow sensor comprising:
a light emitter placed at a first end of a housing;
a light detector placed at a second end of the housing;
the housing defining a flow path in which a fluid moves in a general direction from one of the first and second ends of the housing to the other of the first and second ends of the housing; and
a diaphragm member placed in the flow path between the emitter and the detector, the diaphragm member opening upon flow through the flow path such that light from the emitter is detected by the detector, the diaphragm member closing upon a low pressure condition in the flow path such that not as much light from the emitter is detected by the detector.

2. The flow sensor of claim 1, wherein the light emitter is selected from the group consisting of: a light emitting diode, an infrared light emitter, a fiber optic source and any combination thereof.

3. The flow sensor of claim 1, wherein the light detector is selected from the group consisting of: a phototransistor, an infrared light detector, a photodiode, a photovoltaic cell and any combination thereof.

4. The flow sensor of claim 1, wherein the diaphragm member includes a characteristic selected from the group consisting of: being flexible, being resilient, being naturally biased, including a septum and any combination thereof.

5. The flow sensor of claim 1, wherein the diaphragm member is opaque.

6. The flow sensor of claim 1, which includes first and second housings, the emitter positioned in the first housing, the detector positioned in the second housing and the member coupled between the first and second housings.

7. The flow sensor of claim 1, which includes at least one electrical component operating with the light emitter or detector, the component selected from the group consisting of: an integrated circuit, a power regulator, an indicating light, a resister, a transistor, a diode and any combination thereof.

8. The flow sensor of claim 1, which includes a first output indicative of a fluid flow state and a second output indicative of a low pressure state.

9. The flow sensor of claim 1, which includes an output that ranges depending on a relative amount of fluid flowing through the flow path.

10. The flow sensor of claim 1, wherein the member is configured to close upon a low pressure condition in the flow path such that light from the emitter is not detected by the detector.

11. The flow sensor of claim 1, wherein the low pressure condition is a zero pressure condition or a less than a cracking pressure condition.

12. A flow sensor comprising:
a diaphragm member placed in a flow path within a housing, the housing having first and second ends and configured such that the flow path extends in a general direction from the first end to the second end, the diaphragm member including a stationary portion and an openable portion;
an emitter located at one of the first and second ends;
a receiver located at the other of the first and second ends;
a first output state caused via operation of the emitter and receiver when the openable portion resides in a first position, the first output state indicative of a first flow state; and
a second output state caused via operation of the emitter and receiver when the openable portion resides in a second position, the second output state indicative of a second flow state.

13. The flow sensor of claim 12, wherein the emitter is a light emitter and the receiver is a light receiver, and wherein the first output state is a no/low light detect state and the first flow state is a no/low pressure state.

14. The flow sensor of claim 12, wherein the first output state is a de-energized state and the first flow state is a no/low pressure state.

15. The flow sensor of claim 12, wherein the first output state is a bottom of an output range state and the first flow state is a no/low pressure state.

16. The flow sensor of claim 12, wherein the first output state is a no electrical flow state and the first flow state is a no/low pressure state.

17. The flow sensor of claim 12, wherein the emitter is a light emitter and the receiver is a light receiver, and wherein the second output state is a light detected state and the second flow state is a fluid flowing state.

18. The flow sensor of claim 12, wherein the second output state is an energized state and the second flow state is a fluid flowing state.

19. The flow sensor of claim 12, wherein the second output state is a top of an output range state and the second flow state is a full flow state.

20. The flow sensor of claim 12, wherein the second output state is an intermediate output of an output range state and the second flow state is an intermediate flow state.

21. The flow sensor of claim 12, wherein the first fluid flow state is a non-alarm state and the second fluid flow state is an alarm state.

22. The flow sensor of claim 12, wherein the first fluid flow state is an alarm state and the second fluid flow state is a non-alarm state.

23. The flow sensor of claim 12, wherein the openable portion is moved from the first position to the second position based on a flow of fluid past the member, the fluid being liquid or gaseous.

24. A medical fluid system comprising:
a valve operable to enable fluid to be delivered to a patient;
a sensor including an emitter, a receiver, and a member having an openable portion, the member placed in and held around its perimeter by a housing, the openable portion residing within the perimeter of the member, the housing defining a flow path in fluid communication with the valve; and
a control scheme operable to signal an alarm based on whether the member resides in a first or a second position and an expected opened/closed state of the valve.

25. The medical fluid system of claim 24, wherein the fluid is selected from the group consisting of: dialysate, blood and any combination thereof.

26. The medical fluid system of claim 24, wherein the valve is operable to enable fluid to be delivered to the patient's peritoneal cavity or to a blood corporeal circuit.

27. The medical fluid system of claim 24, wherein the member is opened from the first position to the second position based on a flow of the fluid past the member.

28. The medical fluid system of claim 24, wherein the fluid is a first fluid, and wherein the member is moved by a second fluid.

29. A flow sensing method comprising the steps of:
establishing a first flow state when an openable portion of a diaphragm member located in a fluid flow path resides in a first position, the diaphragm member and fluid flow path located within a housing, the housing having first and second ends and configured such that the fluid flow path extends in a general direction from the first end to the second end;
locating a source at one of the first and second ends;
locating a receiver at the other of the first and second ends; and
establishing a second fluid flow state when a force due to a flow of a fluid through the path causes the openable portion of the diaphragm member to move to a second positions, changing a level of communication between the source and receiver.

30. The flow sensing method of claim 29, wherein establishing the first flow state includes determining that a low pressure condition exists.

31. The flow sensing method of claim 29, wherein establishing the second flow state includes determining that the fluid is flowing within the flow path.

32. The flow sensing method of claim 29, wherein the source is a light source and the receiver is a light receiver, and wherein establishing the first flow state includes detecting at least a relatively low amount of light from a light source and establishing the second flow state includes detecting a relatively high amount of light from the light source.

33. The flow sensing method of claim 29, wherein establishing the first flow state includes not making an electrical connection and establishing the second flow state includes making the electrical connection.

34. The flow sensing method of claim 29, wherein establishing the first flow state includes making an electrical connection and establishing the second flow state includes unmaking the electrical connection.

35. The flow sensing method of claim 29, which includes disabling at least one flow component by establishing the first fluid flow state.

36. The flow sensing method of claim 29, which includes enabling at least one flow component by establishing the second fluid flow state.

37. The flow sensing method of claim 29, which includes enabling at least one flow component by establishing the first fluid flow state.

38. The flow sensing method of claim 29, which includes disabling at least one flow component by establishing the second fluid flow state.

* * * * *